United States Patent
Takasahara et al.

(10) Patent No.: US 10,207,019 B2
(45) Date of Patent: Feb. 19, 2019

(54) ION GENERATOR

(71) Applicant: Sharp Kabushiki Kaisha, Sakai, Osaka (JP)

(72) Inventors: Toshihisa Takasahara, Sakai (JP); Yasutaka Kataoka, Sakai (JP); Akira Yamamoto, Sakai (JP)

(73) Assignee: SHARP KABUSHIKI KAISHA, Sakai, Osaka (JP)

( * ) Notice: Subject to any disclaimer, the term of this patent is extended or adjusted under 35 U.S.C. 154(b) by 0 days.

(21) Appl. No.: 15/504,076

(22) PCT Filed: Sep. 3, 2015

(86) PCT No.: PCT/JP2015/075096
§ 371 (c)(1),
(2) Date: Feb. 15, 2017

(87) PCT Pub. No.: WO2016/067743
PCT Pub. Date: May 6, 2016

(65) Prior Publication Data
US 2017/0274113 A1 Sep. 28, 2017

(30) Foreign Application Priority Data

Oct. 31, 2014 (JP) .................................. 2014-223112
Mar. 13, 2015 (JP) .................................. 2015-050191

(51) Int. Cl.
*A61L 9/22* (2006.01)
*H01T 23/00* (2006.01)

(52) U.S. Cl.
CPC ................ *A61L 9/22* (2013.01); *H01T 23/00* (2013.01); *A61L 2209/11* (2013.01); *A61L 2209/14* (2013.01)

(58) Field of Classification Search
CPC .... A61L 9/22; A61L 2209/11; A61L 2209/14; H01T 23/00
See application file for complete search history.

(56) References Cited

U.S. PATENT DOCUMENTS

2006/0024197 A1* 2/2006 Park .......................... A61L 2/02
422/29

FOREIGN PATENT DOCUMENTS

| JP | 2004-014249 A | 1/2004 |
| JP | 2004-022195 A | 1/2004 |
| JP | 2009-224280 A | 10/2009 |

OTHER PUBLICATIONS

Official Communication issued in International Patent Application No. PCT/JP2015/075096, dated Nov. 24, 2015.

* cited by examiner

Primary Examiner — Timothy C Cleveland
(74) Attorney, Agent, or Firm — ScienBiziP, P.C.

(57) ABSTRACT

Provided is a compact ion generator. A control substrate (30) and an ion generating section (41) are provided concentrically around a motor (31) without overlapping each other, which motor (31) is configured to cause a fan (33) to rotate. The fan (33) is configured to send, more outwards than a radial direction, air sucked in from a side of a first direction which is along a rotational axis direction. A fan cover (50) has (i) a first air flow path (52) configured to guide, in the radial direction, the air sent by the fan (33) and (ii) a second air flow path (53) configured to cause the air, which has been guided by the first air flow path (52) to flow in the radial direction, to be sent towards the side of the first direction. The ion generating section (41) constitutes a part of a wall of the first air flow path (52).

5 Claims, 10 Drawing Sheets

ION GENERATOR

TECHICAL FIELD

The present invention relates to an ion generator which causes an atmospheric discharge so that ions are generated and diffuses the ions in a room.

BACKGROUND ART

There have been conventionally known various ion generators such as (i) a negative ion generator which causes negative ions to be released so that a forest bathing effect is brought about and (ii) a Plasmacluster (Registered Trademark) ion generator which causes negative ions and positive ions to be released so that a bacteria removing effect and a deodorizing effect are bought about.

For example, Patent Literature 1 discloses a lighting device which includes a negative ion generator.

CITATION LIST

Patent Literature

[Patent Literature 1]
Japanese Patent Application Publication Tokukai No. 2004-22195 (Publication Date: Jan. 22, 2004)

SUMMARY OF INVENTION

Technical Problem

A technique disclosed in Patent Literature 1, however, suffers from an increase in size, in an axis direction, of a device. This is because it employs (i) an axial fan and (ii) a negative ion generator which is provided so as to be axially opposite to the axial fan. In a case where the negative ion generator disclosed in Patent Literature 1 is provided on, for example, a ceiling, it takes up lots of space in a direction vertical to a surface of the ceiling. This causes an oppressive feeling to people around the negative ion generator and/or causes a decrease in efficiency of spatial utilization.

The present invention has been attained in view of the above problem, and an object of the present invention is to provide an ion generator which is thin and compact.

Solution to Problem

An ion generator in accordance with an aspect of the present invention includes: a fan configured to send, more outwards than a radial direction, air sucked in from a side of a first direction which is along a rotational axis direction; a motor configured to cause the fan to rotate; an ion generating section configured to generate ions in the sucked air sent by the fan; and a control substrate configured to control at least the motor and the ion generating section, the control substrate, the motor, and the ion generating section being provided concentrically around a rotation axis of the motor without overlapping each other when viewed from the side of the first direction.

An ion generator in accordance with an aspect of the present invention further includes: a fan cover having a first air flow path and a second air flow path, the first air flow path being configured to guide, in the radial direction, air sent from the fan, the second air flow path being configured to cause the air guided via the first air flow path to be sent towards the side of the first direction, the ion generating section constituting a part of a surface of the first air flow path on a side of a second direction, the second direction being opposite to the first direction.

An ion generator in accordance with an aspect of the present invention, wherein the ion generating section is composed of a plurality of ion generating sections, further includes: an ion generating unit in which the plurality of ion generating sections are integrated with each other, the ion generating unit being integrally attachable to and detachable from the fan cover.

An ion generator in accordance with an aspect of the present invention further includes: a housing in which the fan cover is housed, the fan cover being attachable to and detachable from the housing while the ion generating unit is being attached to the fan cover.

An ion generator in accordance with an aspect of the present invention further includes: a lower cover attached to the fan cover on the side of the first direction and having an opening whose shape matches a suction opening of the fan cover; the fan cover having the suction opening via which external air is sucked in and which is provided on the fan cover on the side of the first direction so as to face the fan; a filter provided so as to cover the opening; and a bottom plate attached to the lower cover on the side of the first direction, the lower cover, the filter, and the bottom plate being integrally attachable to and detachable from the fan cover.

An ion generator in accordance with an aspect of the present invention further includes: a duct plug via which the ion generator is connected to a wiring duct, the duct plug being provided so as to be closer to the side of the second direction than the fan.

Advantageous Effects of Invention

In the above configuration, the control substrate and the ion generating section are provided concentrically around the rotation axis of the motor without overlapping each other, which motor is configured to cause the fan to operate. This reduces the ion generator in thickness, and ultimately makes it possible to downsize the ion generator.

In the above configuration, the control substrate and the ion generating section are provided concentrically around the motor, which is the heaviest component of the ion generator. This makes it easier to cause the ion generator to have a weight balanced in vertical and horizontal directions.

With the above configuration, it is possible to provide the motor, which is the heaviest component of the ion generator, near the duct plug via which the ion generator is hung from a ceiling. Thus, even in a case where the ion generator hung from the ceiling is shaken right and left, large torque is less likely to be applied to the duct plug. This allows the ion generator to have a shock-resistant structure.

In the above configuration, the ion generating section constitutes a part of a surface of the first air flow path, which is of the fan cover surrounding the fan and which is configured to guide, in the radial direction of the fan, the air sent by the fan, on a side opposite to an air suction side (i.e., opposite to the side of the first direction) of the fan. This makes it possible to set the air flow path to be shorter as compared with the case where an ion generator is provided so as to be axially opposite to a fan, and ultimately makes it possible to downsize the ion generator.

With the above configuration, it is possible to integrally detach the plurality of ion generating sections, as a part of the ion generating unit, from the fan cover. This allows an improvement in maintenance easiness such as cleaning easiness and replace easiness of the plurality of ion generating sections.

The above configuration includes the housing which covers the fan cover, and makes it possible to integrally detach the fan cover and the ion generating unit from the housing. This allows an improvement in maintenance easiness such as cleaning easiness of the ion generator.

The above configuration makes it possible to integrally attach and detach the lower cover, the filter, and the bottom plate to/from the fan cover, the lower cover corresponding to the suction opening of the fan cover. This allows an improvement in maintenance easiness of the ion generator.

Figure 1:
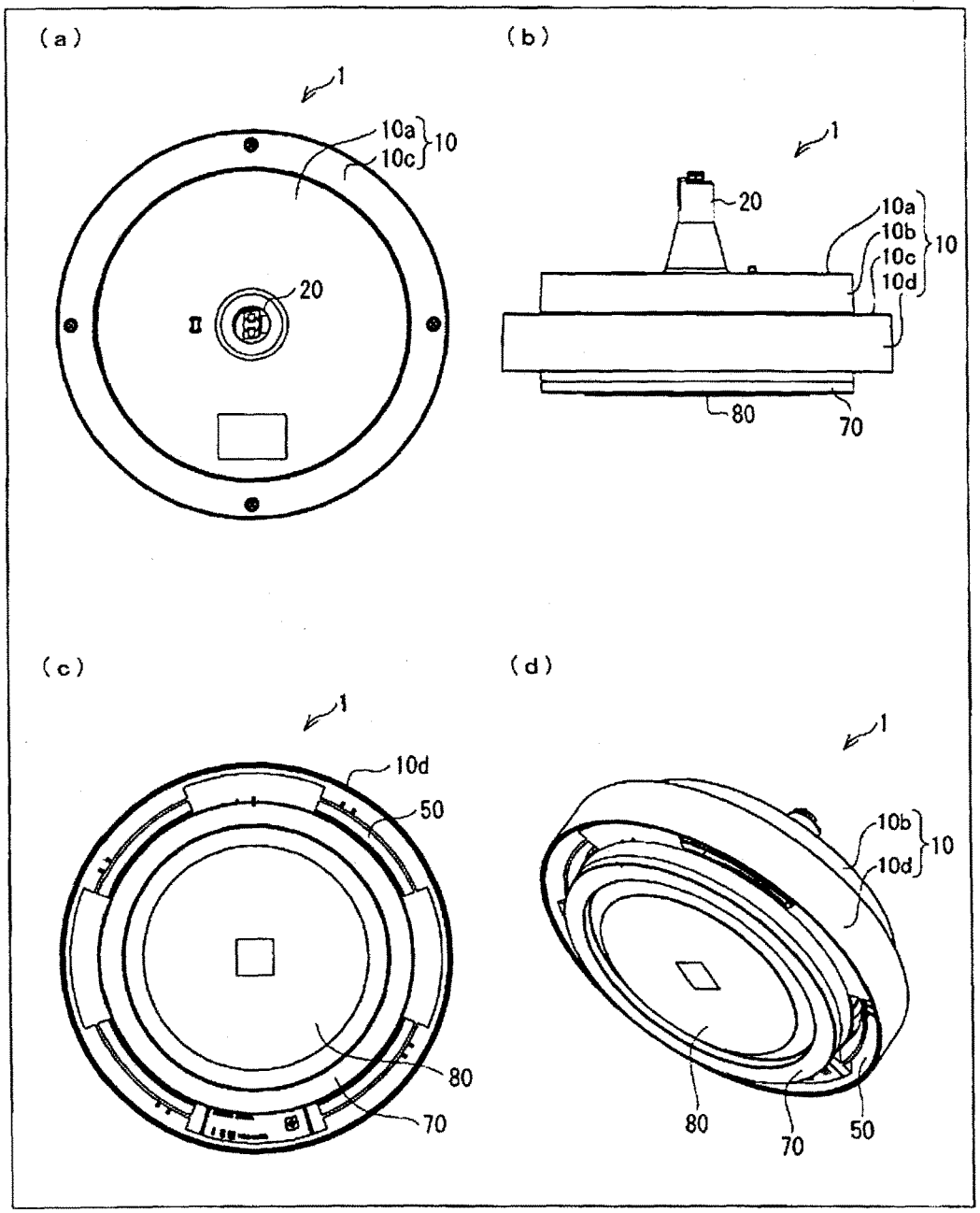
FIG. 1 is a view illustrating an appearance of an ion generator in accordance with Embodiment 1 of the present invention. (a) of FIG. 1 is a top view, (b) of FIG. 1 is a lateral view, (c) of FIG. 1 is a bottom view, and (d) of FIG. 1 is a perspective view of the ion generator.
Figure 5:
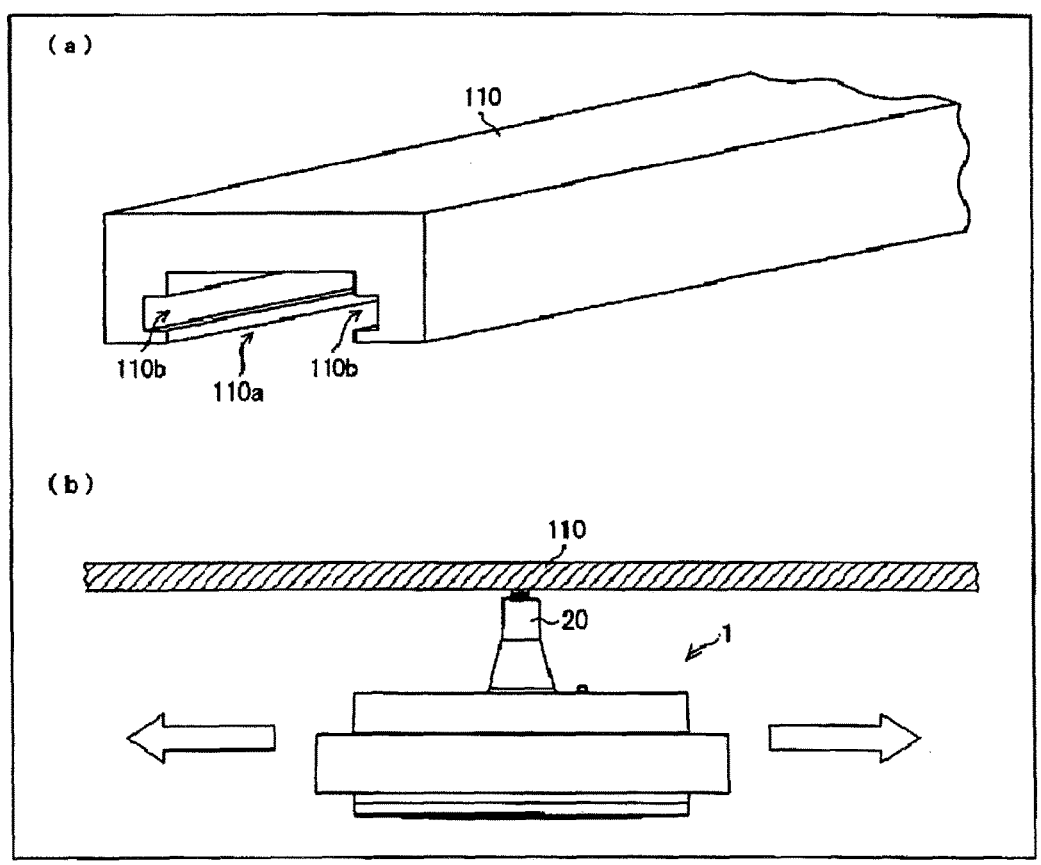

(a) of FIG. 5 is an explanatory view illustrating a configuration of a wiring duct to which the ion generator illustrated in FIG. 1 is to be connected. (b) of FIG. 5 is an explanatory view illustrating how the ion generator illustrated in FIG. 1 is to be connected to the wiring duct illustrated in (a) of FIG. 5.

Figure 6:
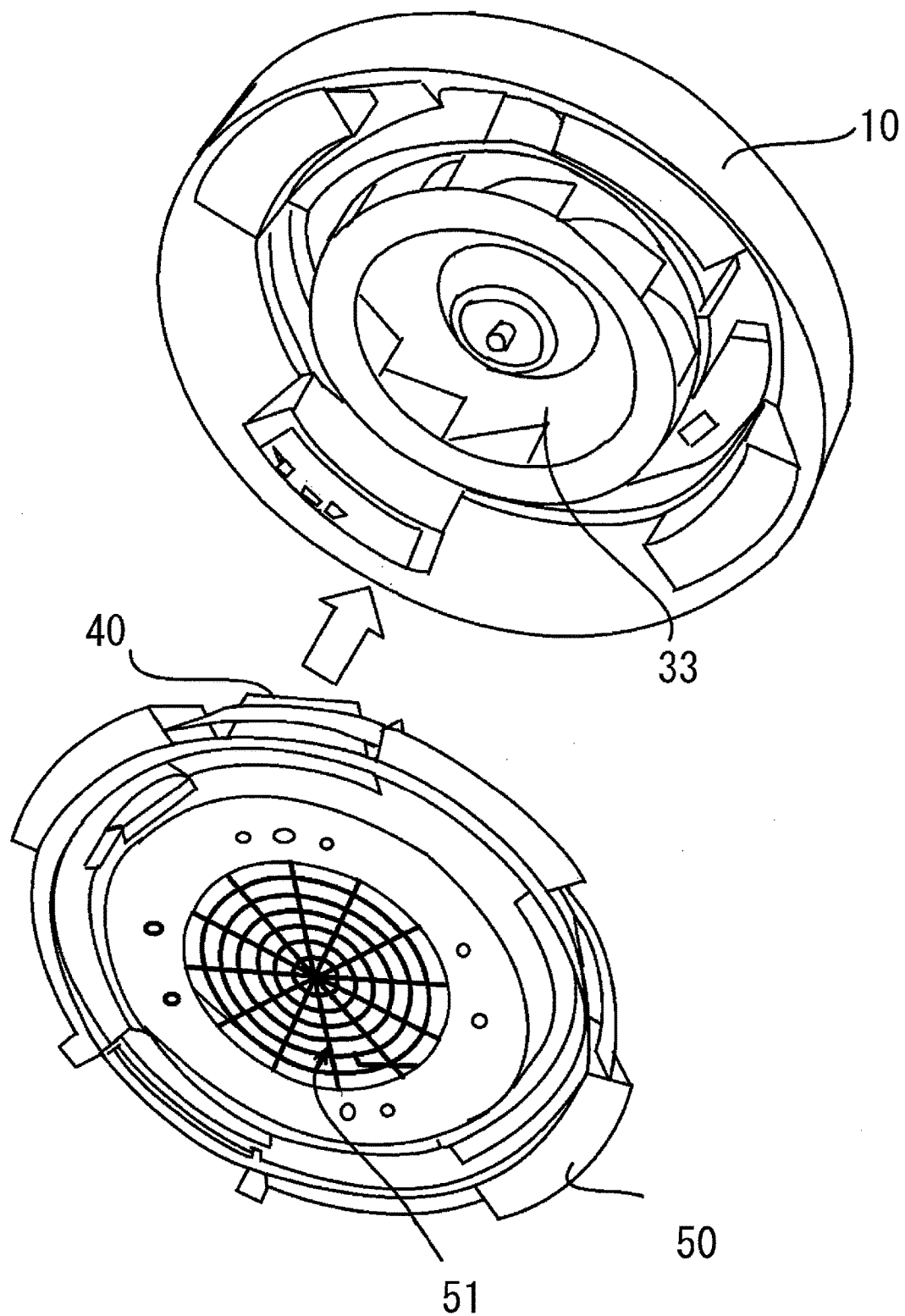

FIG. 6 is an explanatory view illustrating a part of the ion generator illustrated in FIG. 1.

Figure 7:
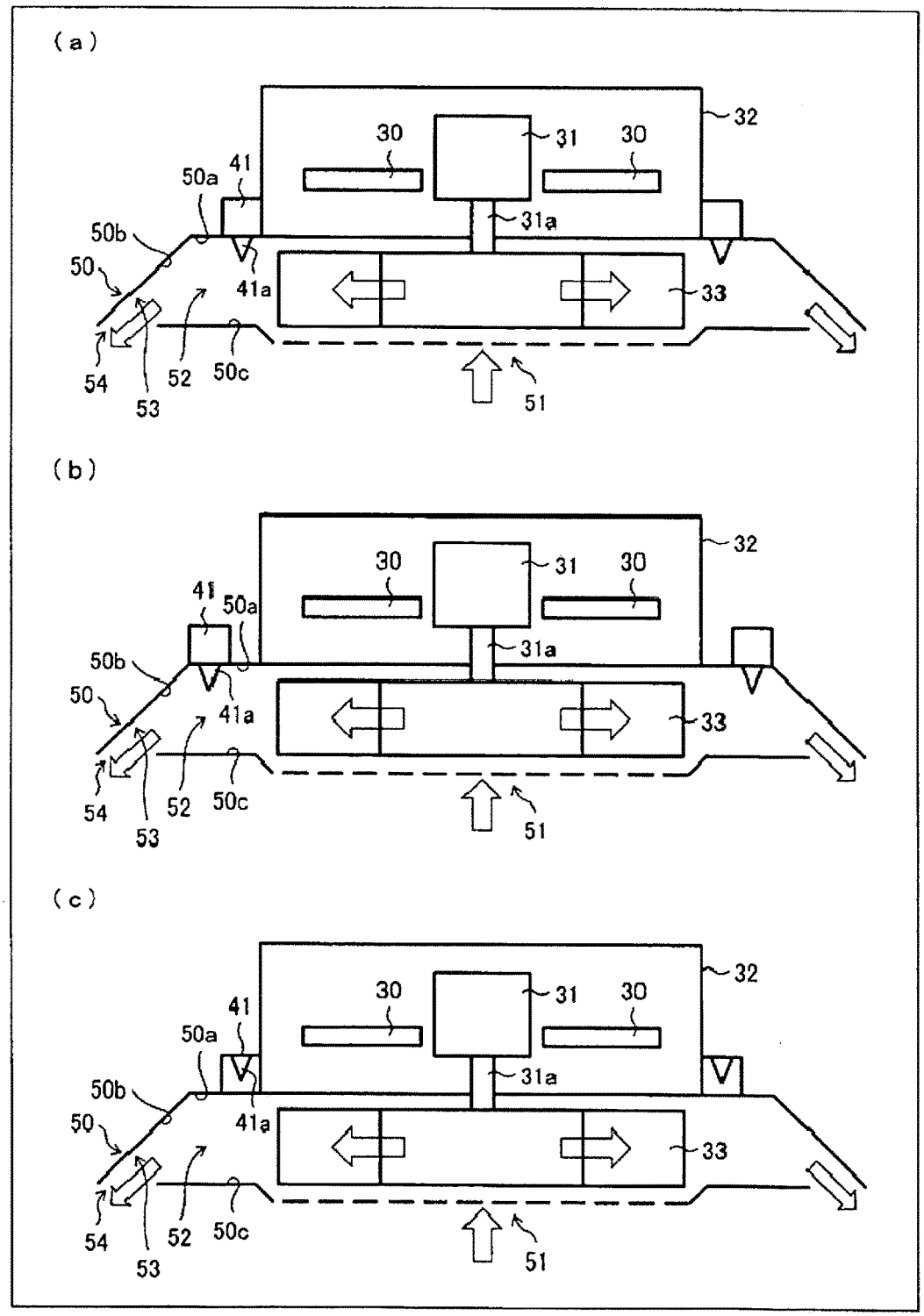

(a) of FIG. 7 is an explanatory view illustrating a relationship between an air flow path, via which air is sent by the fan, and an ion generating section of the ion generator illustrated in FIG. 1. (b) and (c) of FIG. 7 are each an explanatory view illustrating a modification of the air flow path.

Figure 8:
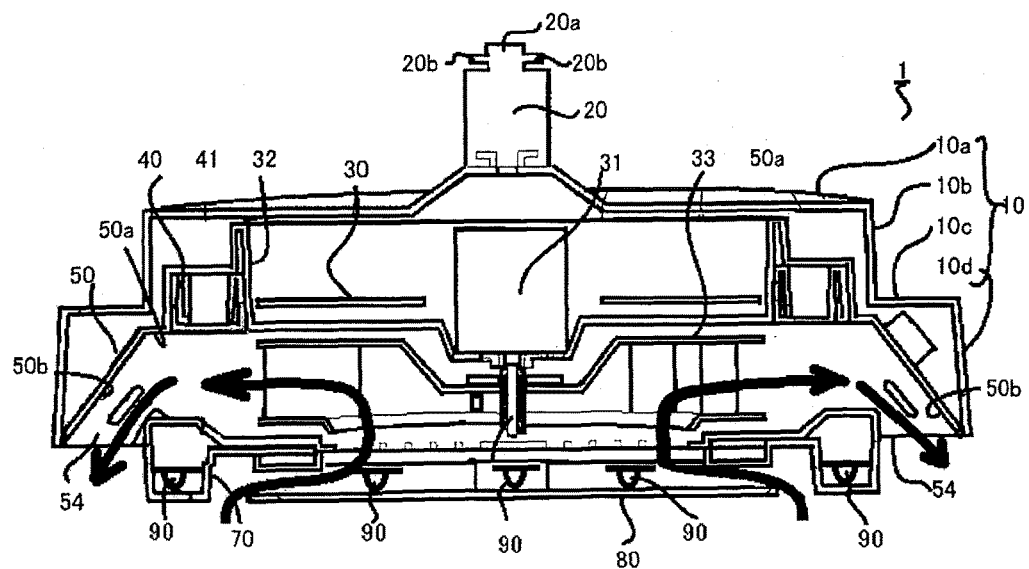

FIG. 8 is a sectional view of an ion generator in accordance with Embodiment 2 of the present invention.

Figure 9:
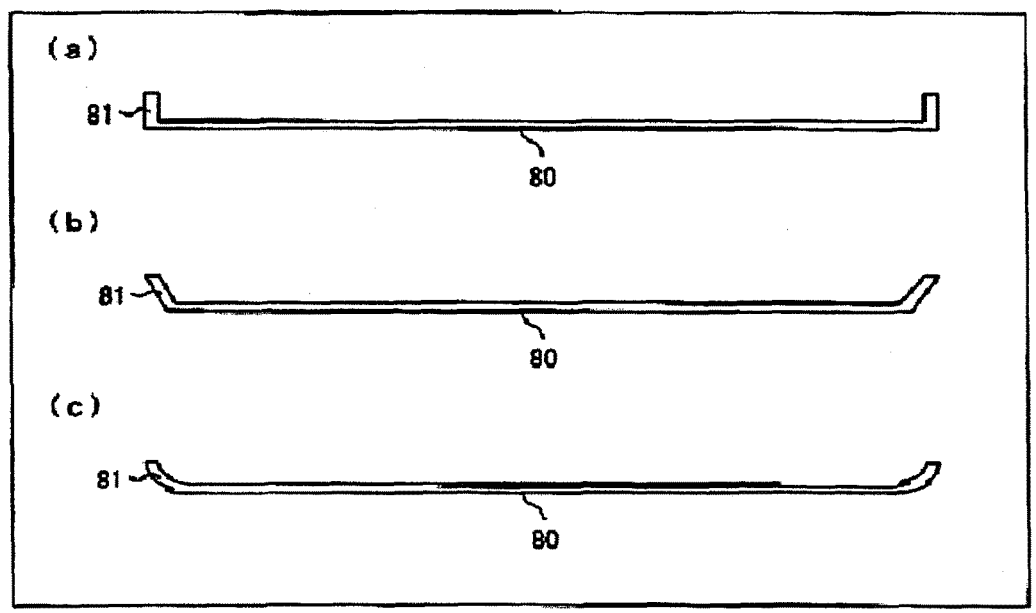

(a) of FIG. 9 is an explanatory view illustrating a configuration of a bottom plate included in an ion generator in accordance with Embodiment 3 of the present invention. (b) and (c) of FIG. 9 are each an explanatory view illustrating a modification of the bottom plate.

Figure 10:
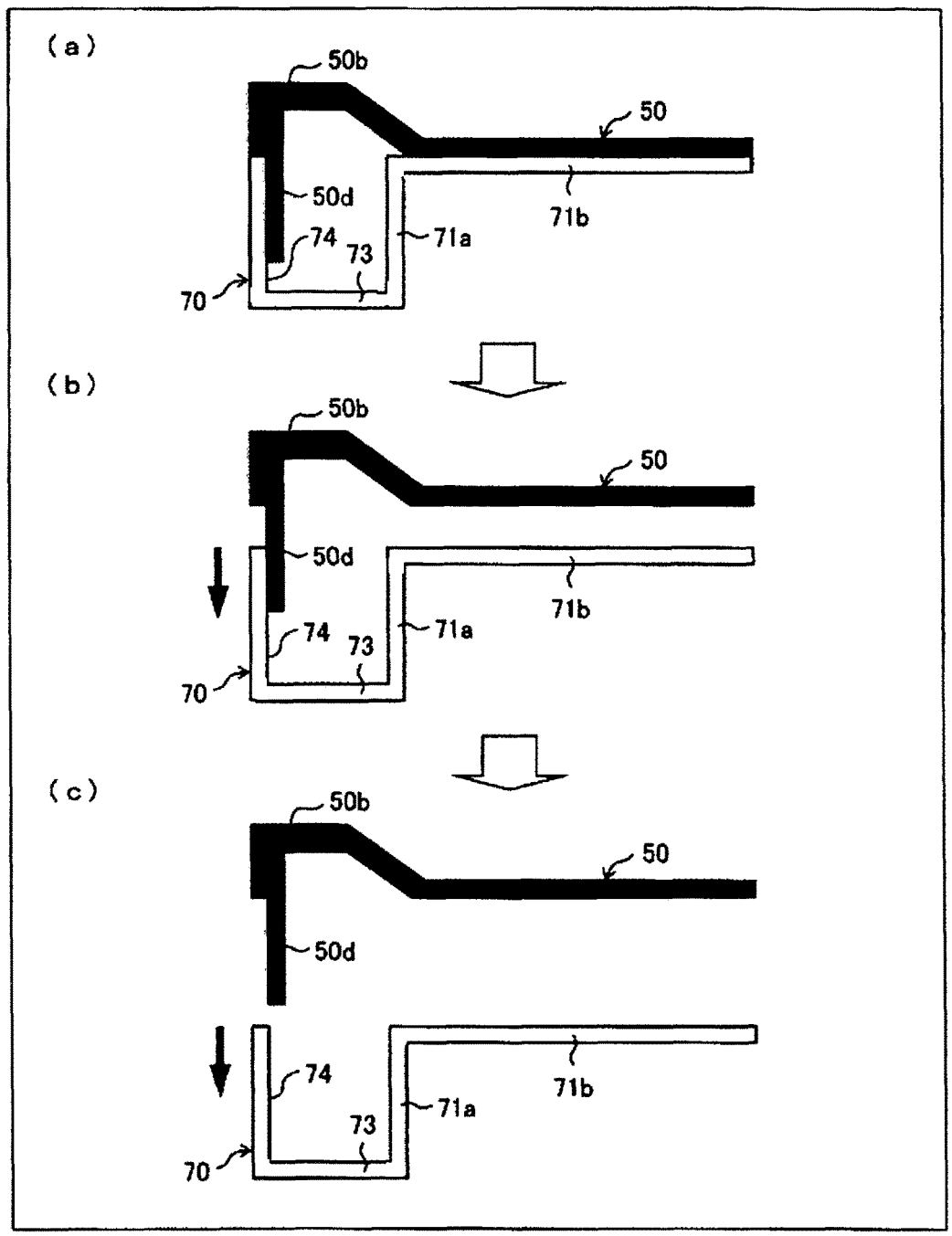

FIG. 10 is an explanatory view illustrating how a fan cover and a lower cover, each of which is included in an ion generator in accordance with Embodiment 4 of the present invention, are brought into contact with each other.

Figure 11:
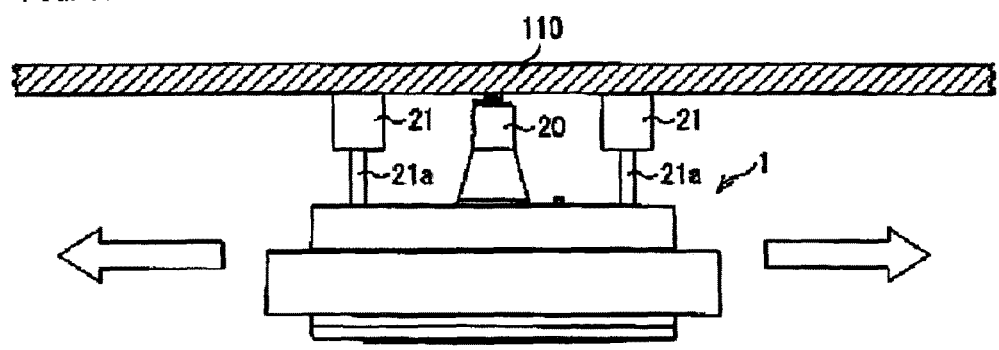

FIG. 11 is an explanatory view illustrating a state where an ion generator in accordance with Embodiment 5 of the present invention is attached to a wiring duct.

Figure 12:
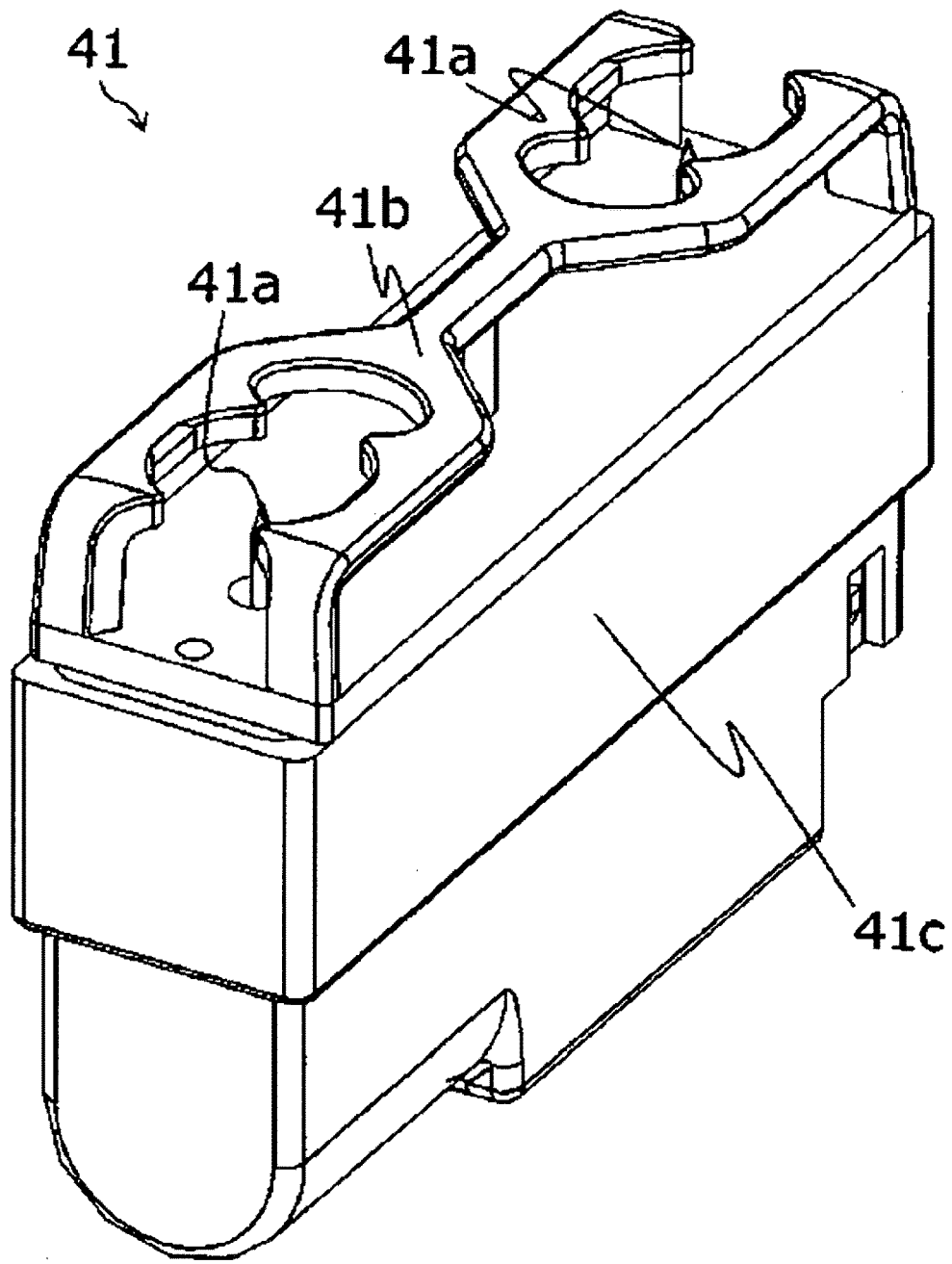

FIG. 12 is a perspective view illustrating a configuration of an ion generating section included in the ion generator illustrated in FIG. 1.

DESCRIPTION OF EMBODIMENTS

[Embodiment 1]

The following description will discuss Embodiment 1 of the present invention with reference to the drawings.

Figure 2:
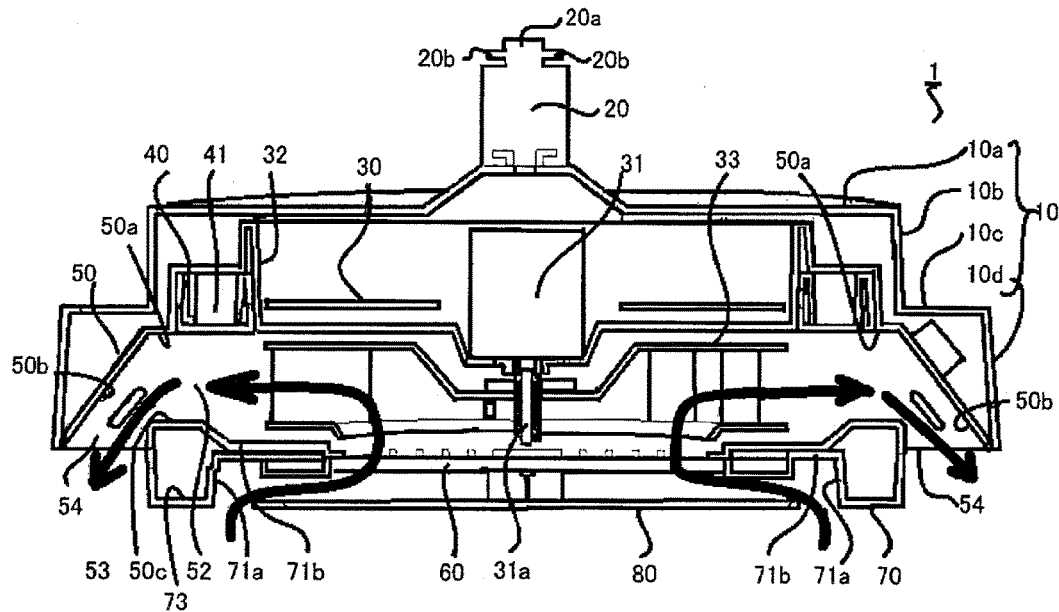
FIG. 2 is a sectional view illustrating an inner structure of the ion generator illustrated in FIG. 1.
Figure 3:
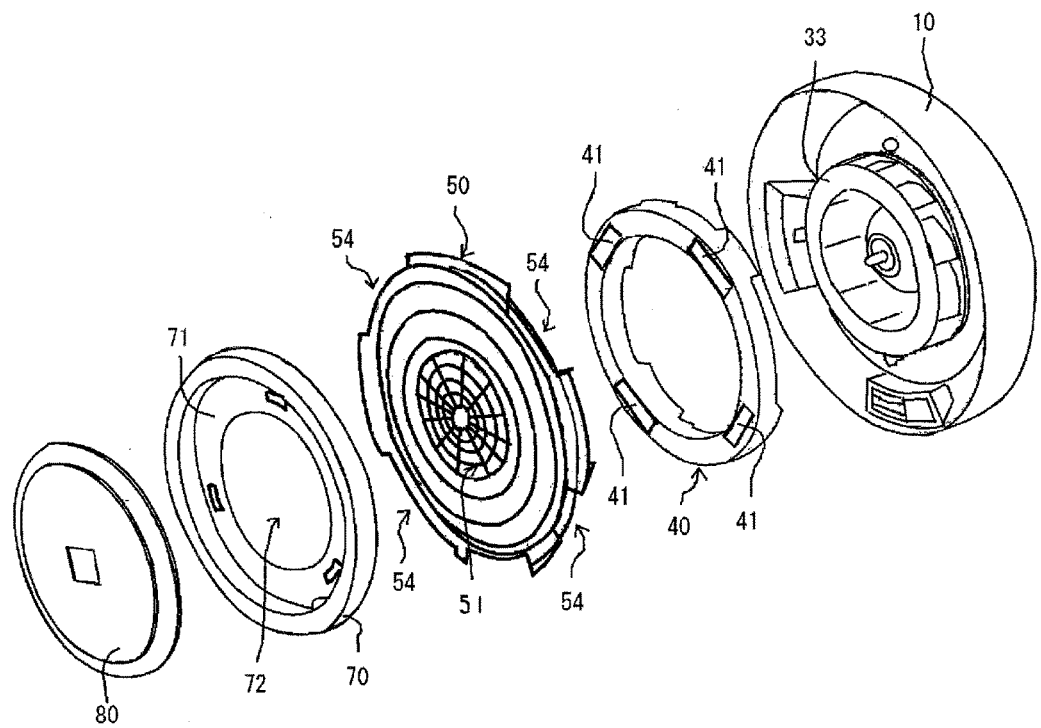
FIG. 3 is an exploded perspective view of the ion generator illustrated in FIG. 1.
Figure 4:
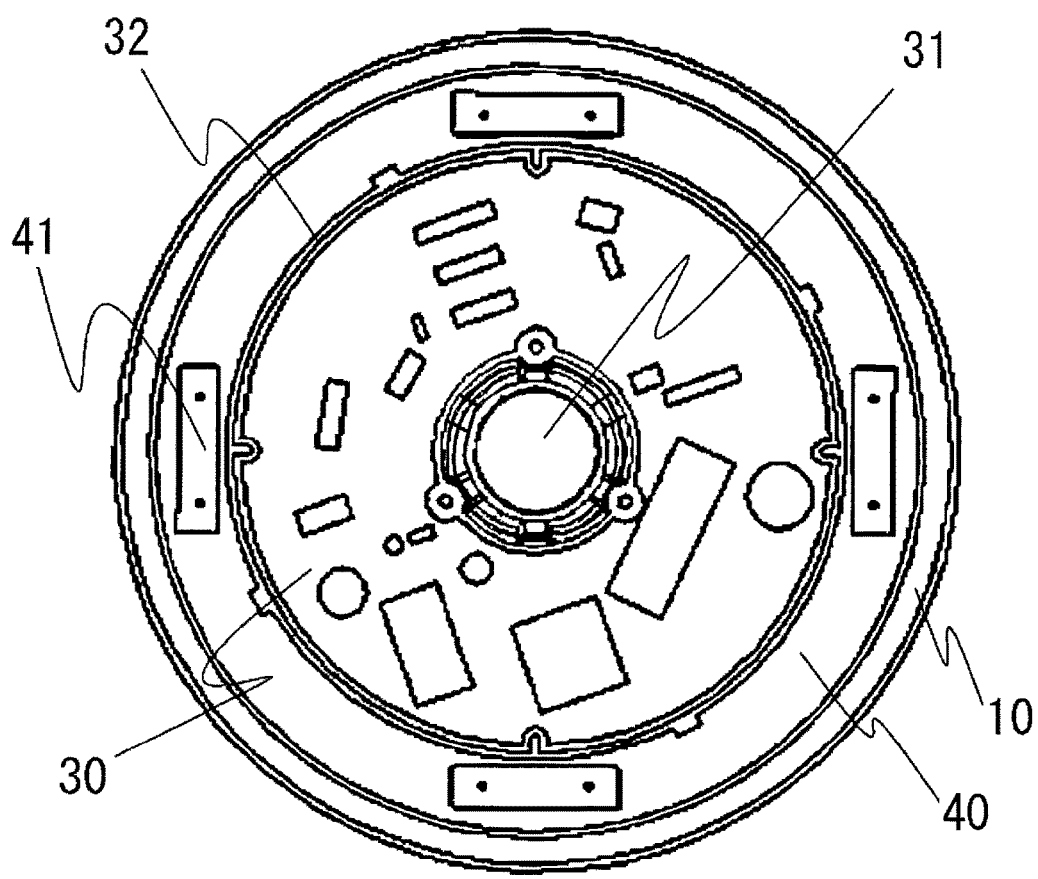
FIG. 4 is a view illustrating how components are provided inside the ion generator illustrated in FIG. 1, the view being obtained in a case where the inside is viewed from a side of a first direction.

FIG. 1 is a view illustrating an appearance of an ion generator 1 in accordance with Embodiment 1. (a) of FIG. 1 is a top view, (b) of FIG. 1 is a lateral view, (c) of FIG. 1 is a bottom view, and (d) of FIG. 1 is a perspective view. FIG. 2 is a sectional view of the ion generator 1. FIG. 3 is an exploded perspective view of the ion generator 1. FIG. 4 is a view illustrating how components are provided inside the ion generator 1, the view being obtained in a case where the inside is viewed from a side of a first direction while a fan is being detached.

As illustrated in FIGS. 1 through 4, the ion generator 1 includes an upper cover (housing) 10, a duct plug 20, a control substrate 30, a motor (fan driving section) 31, a substrate holder 32, a fan (centrifugal fan) 33, a PCI unit (ion generating unit) 40, an ion generating section 41, a fan cover 50, a filter 60, a lower cover 70, and a bottom plate 80.

The upper cover 10 is a member constituting an upper surface of and a side surface of an outer envelope of the ion generator 1. The upper cover 10 includes (i) a first top surface part 10a having a substantially discoid shape, (ii) a first circumferential surface part 10b having an annular shape and extending downwards from a lower end of the first top surface part 10a, (iii) a second top surface part 10c having an annular shape and extending substantially in a horizontal direction from a lower end of the first circumferential surface part 10b, and (iv) a second circumferential surface part 10d having an annular shape and extending downwards from a lower end of the second top surface part 10c. The first top surface part 10a, the first circumferential surface part 10b, the second top surface part 10c, and the second circumferential surface part 10d are each made of a plate member, and the parts 10a through 10d surround a hollow space. Note that each part of the upper cover 10 is not limited in terms of material to any particular one, and can be made of, for example, a resin or a metal.

The duct plug 20 is attached to the first top surface part 10a of the upper cover 10 so as to protrude upwards from around a center of the first top surface part 10a. As illustrated in FIG. 2, the duct plug 20 has, in an end part thereof, (i) a protruding part 20a protruding upwards and (ii) an engaging part 20b, having a discoid shape, which is a part of the protruding part 20a and protrudes in the horizontal direction.

(a) of FIG. 5 is an explanatory view illustrating a schematic configuration of a wiring duct 110 configured to be attached to a ceiling. As illustrated in (a) of FIG. 5, the wiring duct 110 has a shape extending in a given direction. The wiring duct 110 is provided so as to have grooves 110a and 110b which match the protruding part 20a and the engaging part 20b, respectively. This causes the protruding part 20a and the engaging part 20b to fit in the grooves 110a and 110b, respectively. As such, the ion generator 1 is movable, in a direction in which the wiring duct 110 extends, while being hung and supported by the wiring duct 110.

The wiring duct 110 and the duct plug 20 further include respective electrical contacts (not illustrated). When the duct plug 20 is fitted in the wiring duct 110, the electrical contacts of the wiring duct 110 and the duct plug 20 come into contact with each other. This causes the ion generator 1 to receive electricity from an external power source (e.g., commercial power source) via the wiring duct 110. The wiring duct 110 and the duct plug 20 are each widely used, and thus their respective detailed explanations are omitted.

The substrate holder 32 has a substantially discoid and hollow shape. The substrate holder 32 is housed in a space surrounded by the first top surface part 10a of and the first circumferential surface part 10b of the upper cover 10, and is fixed to the upper cover 10.

The substrate holder 32 houses therein (i) the control substrate 30, which includes a control section (not illustrated) configured to control an operation of each part of the ion generator 1, and (ii) the motor 31.

The motor 31 is provided in a through hole which is provided at a center part of the control substrate 30, and has a motor shaft 31a protruding downwards. A fan 33 is attached to the motor shaft 31a. With the configuration, the motor 31 causes, in accordance with instructions supplied from the control section, the motor shaft 31a to rotate so that the fan 33 rotates around the motor shaft 31a.

The fan 33, which is a turbofan (centrifugal fan), is configured to send, more outwards than a radial direction, air sucked in from below (side of the first direction which is along a rotational axis direction). The fan 33 is not limited to such a centrifugal fan, provided that it can send, in the radial direction, air sucked in from below.

The PCI unit 40 has a substantially cylindrical doughnut shape, and is provided between an outer circumferential surface of the substrate holder 32 and an inner surface of the first circumferential surface part 10b of the upper cover 10. On the PCI unit 40, a plurality of ion generating sections 41 (for example, four ion generating sections 41 in case of Embodiment 1) are provided in a circumferential direction at equal intervals.

FIG. 12 is a perspective view illustrating a configuration of the ion generating section 41. As illustrated in FIG. 12, the ion generating section 41 includes an electrode (discharging electrode, discharging section) 41a, a protection arm 41b, and a main body 41c. The electrode 41a and the protection arm 41b are each provided so as to protrude from a lower end surface of the PCI unit 40. The electrode 41a is a projection having a needle-shaped tip. When a high voltage is applied to the electrode 41a, ions are generated from the tip of the electrode 41a.

The PCI unit 40 is designed to have an inner diameter greater than a diameter of the fan 33. Since the fan 33 sends air, which has been sucked therein, more outwards than the radial direction, the electrode 41a of the ion generating section 41 is provided in a lee of an outer circumference of the fan 33. This allows the PCI unit 40 to be detached without detaching the fan 33, and ultimately allows an improvement in maintenance easiness (cleaning easiness) of the ion generating section 41. Furthermore, since the electrode 41a of the ion generating section 41 is provided in the lee of the fan 33, ions generated by the electrode 41a are sent on air currents.

The PCI unit 40 supports and houses therein the ion generating section 41. The PCI unit 40 is a structure intended to facilitate cleaning and replacing of the ion generating section 41, but is not necessarily provided. Alternatively, a structure can be employed in which the ion generating section 41 is directly attached to the fan cover 50.

The ion generating section 41 is configured to cause an atmospheric discharge so that (i) positive ions $H^+(H_2O)m$ (m is a given natural number) which are referred to as Plasmacluster (Registered Trademark) ions and (ii) negative ions $O_2^-(H_2O)n$ (n is a given natural number) are generated and emitted in an atmosphere. The plasmacluster ion is known to have a bacteria removing effect, a deodorizing effect, a virus inhibiting effect, and a static electricity preventing effect. Note that the ion generating section 41 is not limited to a particular configuration, provided that it can emit plasmacluster ions or negative ions in air. For example, a conventionally well-known configuration can be employed as the ion generating section 41.

Alternatively, an electrostatic atomization device for generating charged fine water droplets can be employed as the ion generating section 41.

The fan cover 50 has a substantially discoid and hollow shape and houses therein the fan 33 so as to protect it. The fan cover 50 guides, more outwards than the radial direction, air sent by the fan 33 so that the air is sent downwards from the vicinity of an end located in the radial direction of the ion generator 1.

The fan cover 50 has an upper surface part 50a, a side surface part 50b, and a bottom surface part 50c. The upper surface part 50a has an annular shape whose outer diameter is substantially equal to an inner diameter of the first circumferential surface part 10b of the upper cover 10. The side surface part 50b is inclined downwards (in the first direction) from a circumferential end of the upper surface part 50a. The bottom surface part 50c faces the upper surface part 50a so as to be away, by a given distance, from the upper surface part 50a. The side surface part 50b has a lower end part whose outer diameter is substantially equal to an inner diameter of the second circumferential surface part 10d of the upper cover 10. The fan cover 50 is housed in a space surrounded by the second circumferential surface part 10d.

The upper surface part 50a of and the bottom surface part 50c of the fan cover 50 are provided so as to (i) face each other across the fan 33 and (ii) be substantially parallel to a radial direction of the fan 33. The upper surface part 50a and the bottom surface part 50c thus function as a pressure container for increasing a pressure of air sent by the fan 33. The upper surface part 50a of the fan cover 50 has openings 52a, each of which causes the electrode 41a of and the protection arm 40b of a corresponding ion generating section 41 to be exposed in the fan cover 50. Each of the opening 52a is plugged up by the main body 41c of the corresponding ion generating section 41 so as to be flush with an inner surface of the upper surface part 50a of the fan cover 50.

The fan cover 50 has, at parts of the upper surface part 50a, a plurality of engaging parts (not illustrated) via which the PCI unit 40 is attached to the upper cover 10. Accordingly, in the PCI unit 40A, a plurality of engaged parts (not illustrate) are provided so as to correspond to and be engaged with the respective plurality of engaging parts. This allows the PCI unit 40 to be attachable to and detachable from the fan cover 50, and the PCI unit 40 is therefore integrated with the upper surface part 50a of the fan cover 50. As such, the ion generating section 41 constitutes a part of the upper surface part 50a.

Furthermore, the upper cover 10 has, at parts thereof, a plurality of attaching parts (not illustrated) via which the fan cover 50 is attached to the upper cover part 10. Accordingly, in the fan cover 50, a plurality of attached parts (not illustrated) are provided so as to correspond to the respective plurality of attaching parts. This causes the PCI unit 40 and the fan cover 50, which has been integrated with each other, to be attached to an inner side of the upper cover 10 (see FIG. 6). This also causes the PCI unit 40 and the fan cover 50 to be detached from the upper cover 10 also while the PCI unit 40 and the fan cover 50 are being integrated with each other.

Note that the plurality of engaging parts and the plurality of engaged parts are not particularly configured as such, provided that they are configured so that the PCI unit 40 is attached to the fan cover 50. Such parts can be achieved by a conventionally well-known configuration such as (i) a configuration in which claw-like members are hooked, (ii) a configuration in which male parts are fitted in respective female parts, or (iii) a configuration in which the PCI unit 40 is screwed. Similarly, the plurality of attaching parts and the plurality of attached parts are not particularly configured, provided that the PCI unit 40 and the fan cover 50, which are integrated with each other, are attached to the upper cover 10.

The fan cover 50 has, at a center part of the bottom surface part 50c, a suction opening 51 via which external air is introduced into the fan cover 50. The fan cover 50 also has, between the bottom surface part 50c and the side surface part 50b, a plurality of discharge openings 54 (openings) (for example, four discharge openings 54 in Embodiment 1) provided, at equal intervals, in the circumferential direction. Note that the suction opening 51 has a lattice structure (mesh structure) having a large number of openings (see FIG. 6).

Embodiment 1 employs a structure in which (i) the ion generating sections 41 and the plurality of discharge openings 54 are provided by identical numbers and (ii) each of the ion generating sections 41 is provided on the upper surface part 50a of the fan cover 50 while being fitted in the PCI unit 40 so as to be provided on a virtual straight line which connects a center of the suction opening 51 to the plurality of discharge openings 54. Such a structure prevents ions, generated by each of the ion generating sections 41, from adhering to surrounding members. This ultimately prevents an amount of generated ions to be released from being reduced.

With the structure, the air sent by the fan 33 is guided, more outwards than the radial direction of the fan 33, via a first air flow path 52 which is provided between the upper surface part 50a of and the bottom surface part 50c of the fan cover 50. The air which has been guided via the first air flow path 52 is caused to flow downwards (towards the side of the first direction) via a second air flow path 53 which is provided between the side surface part 50b and the bottom surface part 50c, and is then sent via the plurality of discharge openings 54. Note that the side surface part 50b is shaped so as to be inclined more downwards than the radial direction of the fan 33 while being twisted in the circumferential direction of the fan 33. This causes the air to be sent downwards and towards the plurality of discharging openings 54.

(a) of FIG. 7 is an explanatory view illustrating how air, sent by the fan 33, flows. White arrows illustrated in (a) of FIG. 7 each indicate flow of air. As illustrated in (a) of FIG. 7, the first air flow path 52 is formed between the upper surface part 50a of and the bottom surface part 50c of the fan cover 50. The first air flow path guides, more outwards than the radial direction, air sent by the fan 33. The second air flow path 53 is formed between the side surface part 50b and the bottom surface part 50c of the fan cover 50. The second air flow path 53 cause the air guided by the first air flow path 52 to be sent more downwards (towards the side of the first direction) than the radial direction of the fan 33. The air which has been caused to be sent downwards by the second air flow path 53 is then sent downwards of the ion generator 1 via the plurality of discharge openings 54, each of which is provided between the lower end of the side surface part 50b and the bottom surface part 50c. The PCI unit 40 is attached to the upper surface 50a so that the ion generating section 41 integrated with the PCI unit 40 constitutes (i) a part of the upper surface part 50a and (ii) a part of the first air flow path 52.

In Embodiment 1, since the ion generating section 41 is provided on the upper surface part 50a of the fan cover 50, a minimum area should be provided to cause a fan 33 to operate. Thus, unlike conventional techniques, it is unnecessary to provide a long air flow path to connect a discharge opening 54 to a part of fan.

In Embodiment 1, the ion generating section 41 includes the needle-shaped electrode 41a having a pointed tip. The tip of the electrode 41a is provided so as to point downwards, i.e., the tip of the electrode 41a points so as to be substantially parallel to the rotational axis direction of the fan 33 (see (a) of FIG. 7). Furthermore, the tip of the electrode 41a is provided so as to protrude from the upper surface 50a inside the first air flow path 52. This makes it possible to send air flow caused by the fan 33 with which air flow ions are mingled.

In a case where the ion generating sections 41 are provided in the vicinity of the outer circumference of the fan 33 as with Embodiment 1, the electrode 41a of the ion generating section 41 is hit by (i) air flow sent by the fan 33 towards the plurality of discharge openings 54 and (ii) air flow sent along a rotation direction of the fan 33 so that the air flow is adhered to a rim part of the fan 33. This causes ions generated by the electrode part 41a to be sent in larger amounts, and ultimately causes an increase in amount of ions to be sent from the plurality of discharge openings 54.

In a configuration illustrated in (a) of FIG. 7, the ion generating section 41 is provided on the upper surface part 50a so as to be nearer to a center of the upper surface 50a (in the vicinity of the substrate holder 32). Note, however, that Embodiment 1 is not limited as such. Alternatively, the ion generating section 41 can be provided, for example, on the upper surface part 50a so as to be located farther from the center of the upper surface part 50a (in the vicinity of the side surface part 50b) (as illustrated in (b) of FIG. 7). Alternatively, the ion generating section 41 can be provided on the upper surface part 50a so as to be located at a center part in a radial direction. Furthermore, in the configuration illustrated in (a) of FIG. 7, the tip of the electrode 41a is provided so as to protrude from the upper surface part 50a inward the first air flow path 52. However, Embodiment 1 is not limited as such. Alternatively, the tip of the electrode 41a can be provided in the ion generating section 41 so as to be located above the upper surface part 50a. The ion generating section 41 is not limited to such a configuration in which the electrode 41a has a pointed tip, provided that the ion generating section 41 can emit plasmacluster ions and/or negative ions.

The lower cover 70 is a member having a substantially annular shape and includes (i) a rim part 73 which is recessed from its upper surface side toward its bottom surface side, (ii) a recess part 71 having a substantially circular shape and provided so as to be nearer to a center of the rim part 73 and so as to be recessed from its bottom surface side to its upper surface side, and (iii) an opening 72 provided at a center of the recess 71. The opening 72 is provided so as to have a shape which matches the suction opening 51 of the fan cover 50 and so as to communicate with the suction opening 51.

The bottom plate 80 has a substantially discoid shape and has an outer diameter which is (i) slightly smaller than that of the recess 71 of the lower cover 70 and (ii) greater than those of the opening 72 and the filter 60. The bottom plate 80 is attached to the lower cover 70 so that a given gap is provided between the bottom plate 80 and respective of (i) a side wall 71a which defines a circumferential end part of the recess 71 and (ii) a bottom surface 71b of the recess 71. A method of attaching the bottom plate 80 to the lower cover 70 is not limited to a particular method. The bottom plate 80 can be attached to the lower cover 70 by, for example, (i) a configuration in which claw-like members are hooked, (ii) a configuration in which male parts are fitted in respective female parts, or (iii) a configuration in which the bottom plate 80 is screwed.

The lower cover 70, to which the filter 60 has been attached so as to cover the opening 72, is attached to the fan cover 50. A method of attaching the lower cover 70 to the fan cover 50 is not limited to a particular method. The lower cover 70 can be attached to the fan cover 50 by, for example, a configuration in which claw-like members are hooked, a configuration in which male parts are fitted with respective female parts, or a configuration in which the lower cover 70 is screwed.

With the above configuration, suction force, caused in response to the fan 33 rotating, causes air to be sucked in from a gap between the bottom plate 80 and the lower cover 70. The air thus sucked in passes through the opening 72 of the lower cover 70, the filter 60, and the suction opening 51 of the fan cover 50, and is then sucked in by the fan 33. Flows of respective air currents are indicated by black arrows illustrated in FIG. 2. The air thus sucked in by the fan 33 is sent by the fan 33 more outwards than the radial direction, is sent through the first air flow path 52 and the second air flow path 53, and is then sent downwards from the plurality of discharge openings 54. Note that, since the ion generating section 41 is provided in the first air flow path 52 located between the fan 33 and the discharge opening 54, the air thus sent from the plurality of discharge openings 54 contains ions generated by the ion generating section 41.

The bottom plate 80 has no air suction opening which is generally provided. It follows that, even in a case where dust adhering to a bottom surface of the filter 60 peels off due to its own weight and/or vibration, it is possible to prevent the dust from falling directly in a room. Furthermore, air flow, which has been sucked in from a rim part of the bottom plate 80, is guided towards a center of the bottom plate 80. This makes it possible to prevent dust, which has flaked away from the filter 60, from falling from the rim part of the bottom plate 80 in a room.

As described above, the ion generator 1 in accordance with Embodiment 1 includes the fan cover 50 having (i) the first air flow path 52 configured to guide, more outwards than the radial direction of the fan 33, air sent by the fan 33 and (ii) the second air flow path 53 configured to change the direction of the air, which has been guided by the first air flow path, to be sent more downwards than the radial direction. The ion generating section 41 is provided so as to constitute a part of an upper surface of the first air flow path 52, i.e., a part of the upper surface part 50*a* of the fan cover 50.

The above configuration makes it possible to downsize an ion generator by reducing a thickness, in an axis direction, of the fan in the ion generator, as compared with a configuration in which an ion generating section is provided so as to be axially opposite to the fan. Furthermore, the PCI unit 40, which includes the ion generating section 41, itself constitutes a part of an air flow path. This makes it possible to efficiently design an air flow path with little loss. It is also possible to reduce the number of components of the ion generator 1, as compared with the case where members constituting an air flow path are provided separately from the PCI unit 40.

In Embodiment 1, the plurality of ion generating sections 41 are integrated with the PCI unit 40. Thus, in a case where the plurality of ion generating sections 41 are to be detached from the ion generator 1 during their cleaning and/or maintenance, it is only necessary to detach the PCI unit 40, with which the plurality of ion generating sections 41 are integrated, instead of removing the plurality of ion generating sections 41 one by one. This makes it possible to safely and easily detach each of the plurality of ion generating sections 41 from the ion generator 1.

In Embodiment 1, the control substrate 30 and the ion generating section 41 are provided in a direction parallel to the radial direction of the fan 33. This makes it possible to further reduce the ion generator 1 in thickness in the rotational axis direction of the fan 33, and ultimately makes it possible to further downsize the ion generator 1.

FIG. 4 illustrates a positional relationship between the control substrate 30, the motor 31, the PCI unit 40, and the ion generating section 41, each of which is included in the ion generator 1 in accordance with Embodiment 1. FIG. 4 is a drawing illustrated when the ion generator 1 is viewed in the first direction so that how the ion generator 1 is internally configured can be seen. FIG. 4 illustrates a state where (i) the fan 33, the filter 60, the lower cover 70, and the bottom plate are detached and (ii) the substrate holder 32 is transparent. Note that locations of the control substrate 30 and the ion generating section 41 in FIG. 4 can be changed, in location, with each other in the radial direction of the fan 33.

In Embodiment 1, the fan cover 50 and the PCI unit 40 are configured so as to be attached to and detached from the upper cover 10 while the PCI unit 40, including the ion generating section 41, is integrated with the fan cover 50. This makes it possible to safely and easily detach the PCI unit 40 and the fan cover 50 from the ion generator 1 during their cleaning and/or maintenance.

In Embodiment 1, (i) the lower cover 70, the filter 60, and the bottom plate 80 can be integrally attached to and detached from the fan cover 50 and (ii) the bottom plate 80 has an outer diameter greater than that of the filter 60. This makes it possible to prevent dust and/or the like adhering to the filter 60 from falling while the lower cover 70, the filter 60, and the bottom plate 80 are being detached from the fan cover 50.

[Embodiment 2]

The following description will discuss Embodiment 2 of the present invention. For convenience, identical reference signs will be given to members each having functions identical to those of members described in Embodiment 1, and description of such members will be omitted.

FIG. 8 is a sectional view of an ion generator 1 in accordance with Embodiment 2. In addition to the configuration of the ion generator 1 in accordance with Embodiment 1, the ion generator 1 in accordance with Embodiment 2 further includes a lighting member 90 configured to emit illumination light towards a lower space. The lighting member 90 is not limited to a specific one, provided that it has a light emitting function such as an electric bulb, an LED, an organic EL, or a fluorescent bulb.

In Embodiment 2, (i) a lower cover 70 and a bottom plate 80 are each made of a material having a light transmitting property and (ii) for example, a plurality of lighting members 90 are provided in an area for a back surface of the lower cover 70 or on a back surface of the bottom plate 80 when the ion generator 1 is viewed from below. Note that the number of the plurality of lighting members 90 is not limited to a particular one and locations of the respective plurality of lighting members 90 are not limited to particular ones. For example, the lighting member(s) 90 can be provided so as to protrude to outside of the ion generator 1.

With the configuration, it is possible that the ion generator 1 has both of an ion emitting function and an illuminating function.

[Embodiment 3]

The following description will discuss Embodiment 3 of the present invention. For convenience, identical reference signs will be given to members each having functions identical to those of members described in Embodiments 1 and 2, and description of such members will be omitted.

(a) of FIG. 9 is a sectional view of a bottom plate 80 included in an ion generator 1 in accordance with Embodiment 3. While Embodiment 1 employs the bottom plate 80 having a substantially discoid shape, Embodiment 3 employs a bottom plate 80 whose rim part 81 is bent upwards. This makes it possible to efficiently prevent dust or the like adhering to a filter 60 from falling.

Note that an angle by which the rim part 81 of the bottom plate 80 is bent is not limited to a particular angle. The rim part 81 can be bent, for example, (i) in a substantially vertical direction as illustrated in (a) of FIG. 9 or (ii) in a direction inclined in a horizontal direction and a vertical direction as illustrated in (b) of FIG. 9. Note that the rim part 81 is not necessarily bent. Alternatively, the rim part 81 of the bottom plate 80 can be inclined upwards so as to have a curvature as illustrated in (c) of FIG. 9.

[Embodiment 4]

The following description will discuss Embodiment 4 of the present invention. For convenience, identical reference signs will be given to members each having functions identical to those of members described in Embodiments 1 through 3, and description of such members will be omitted.

(a) through (c) of FIG. 10 are each an explanatory view illustrating how a fan cover 50 and a lower cover 70, each of which is included in an ion generator 1 in accordance with Embodiment 4, are brought into contact with each other. As illustrated in FIG. 10, the lower cover 70 has a guided surface 74 which is provided so as to be parallel to a vertical direction when the lower cover 70 is attached to the fan cover 50. Accordingly, the fan cover 50 has, at a location corresponding to the guided surface 74, a guide 50d configured to regulate the lower cover 70 to move in a vertical direction when the lower cover 70 is to be attached to or detached from the fan cover 50.

With the configuration, in a case where a user attempts to integrally attach or detach the lower cover 70, a filter 60, and a bottom plate 80 to or from the fan cover 50, the user can move the lower cover 70, the filter 60, and the bottom plate 80 straight in the vertical direction without intention. This makes it possible to efficiently prevent dust or the like adhering to the filter 60 from falling.

The guided surface 74 illustrated in FIG. 10 is provided around a rim part of the lower cover 70. Note, however, that a location of the guided surface 74 is not particularly limited, provided that the guided surface 74 is located so as to regulate a movement direction of the lower cover 70.

[Embodiment 5]

The following description will discuss Embodiment 5 of the present invention. For convenience, identical reference signs will be given to members each having functions identical to those of members described in Embodiments 1 through 4, and description of such members will be omitted.

FIG. 11 is an explanatory view illustrating a state where an ion generator 1 in accordance with Embodiment 5 is connected to a wiring duct 110. As illustrated in FIG. 11, the ion generator 1 in accordance with Embodiment 5 includes, in addition to a duct plug 20, two dummy duct plugs 21 each of which is attached to an upper cover 10 via a corresponding one of connecting parts 21a. The ion generator 1 is thus attached to the wiring duct 110, at three locations in total, that is, via the duct plug 20 and the two dummy duct plugs 21.

As with the duct plug 20, a part of each of the dummy duct plugs 21, at which part the each of the dummy duct plugs 21 is connected to the wiring duct 110, has a shape which matches a groove 110a or 110b of the wiring duct 110. With the configuration, it is possible to move the ion generator 1 in a direction in which the wiring duct 110 extends, as with the case where an ion generator 1 is connected to a wiring duct 110 via a single duct plug 20. Note, however, that an electrical connection, via the wiring duct 110, between the ion generator 1 and an external power source is made by only using the duct plug 20, and thus the dummy duct plugs 21 are not involved in such an electrical connection via the wiring duct 110.

With the configuration, it is possible to connect the ion generator 1 to the wiring duct 110 at a plurality of locations. This ultimately allows the ion generator 1 to be more stably supported by the wiring duct 110, as compared with a case where an ion generator 1 is connected to a wiring duct 110 via a single duct plug 20. This allows an improvement in resistance of the ion generator 1 against rolling and the like, and ultimately allows a more secure prevention of the ion generator 1 from falling.

The dummy duct plugs 21 are each similar to the duct plug 20 except that each of them does not have an electrical contact. Thus, the dummy duct plugs 21 each can be approximately made identical to the duct plug 20 in shape. This allows a reduction in sense of discomfort, in appearance, caused by the dummy duct plugs 21.

The above configuration also eliminates the need for taking measures, such as screwing the ion generator 1 to a wall or a ceiling, in order to prevent the ion generator 1 from falling. This makes it possible to prevent the ion generator 1 from falling without impairing a user's convenience and/or an appearance of an existing equipment.

Note that a material of and a shape of each of the connecting parts 21a are not limited to particular ones. Each of the connecting parts 21a can be a member made of a resin or a metal, and can alternatively be a member having a string shape or a wire shape. Furthermore, each of the connecting parts 21a can be fixed to the upper cover 10 or can alternatively be attachable to and detachable from the upper cover 10. Alternatively, each of the dummy duct plugs 21 can be fixed to a corresponding one of the connecting parts 21a or can alternatively be attachable to and detachable from the corresponding one of the connecting parts 21a.

Embodiment 5 has discussed a configuration in which the two dummy duct plugs 21 are provided. Note, however, that the number of the dummy duct plugs 21 is not particularly limited as such.

[Main Points]

An ion generator 1 in accordance with a first aspect of the present invention includes: a fan 33 configured to send, more outwards than a radial direction, air sucked in from a side of a first direction which is along a rotational axis direction; and an ion generating section 41 configured to generate ions in the air sent by the fan 33, a control substrate 30 and the ion generating section 41 being provided concentrically around a motor 31 without overlapping each other as an inner structure of the ion generator 1 being viewed from the side of the first direction, the motor 31 being configured to cause the fan 33 to rotate.

In the above configuration, the control substrate 30 and the ion generating section 41 are provided concentrically around the motor 31 without overlapping each other. This makes it possible to reduce the ion generator in thickness, and ultimately makes it possible to downsize the ion generator.

The ion generator 1 in accordance with the first aspect of the present invention includes: the fan 33 configured to send, more outwards than the radial direction, air sucked in from the side of the first direction which is along the rotational axis direction; the ion generating section 41 configured to generate ions in the air sent by the fan 33; and a fan cover 50 having a first air flow path 52 and a second air flow path 53, the first air flow path 52 being configured to guide, in the radial direction, the air sent by the fan 33, the second air flow path 53 being configured to cause the air guided via the first air flow path 52 to be sent towards the side of the first direction, the ion generating section 41 constituting a part of a surface (upper surface 50*a*) of the first air flow path 52 on a side of a second direction, the second direction being opposite to the first direction.

In the above configuration, the ion generating section 41 is provided on a part of the upper surface 50*a* of the first air flow path 52, which surface is opposite to an air suction side (the side of the first direction), the first air flow path 52 being configured to guide, in the radial direction of the fan 33, air sent by the fan 33. This makes it possible to reduce the ion generator in thickness as compared with the case where an ion generating section is provided so as to be axially opposite to a fan, and ultimately makes it possible to downsize the ion generator.

An ion generator 1 in accordance with a second aspect of the present invention is arranged such that, in the first aspect of the present invention, the ion generating section 41 is composed of a plurality of ion generating sections 41 provided, at given intervals, in a circumferential direction of the fan 33.

In the above configuration, the plurality of ion generating sections 41 are provided, at given intervals, in the circumferential direction of the fan 33 and around the motor 31 having a large mass. This makes it possible to cause ions to be uniformly generated in air to be sent from the ion generator 1. Furthermore, since the plurality of ion generating sections 41 are provided at the given intervals, it is easier to cause the ion generator 1 to have a weight balanced around the motor 31. This makes it possible to stabilize a center of gravity of the ion generator 1.

An ion generator 1 in accordance with a third aspect of the present invention, wherein the ion generation section 41 is composed of a plurality of ion generating sections 41, further includes, in the second aspect of the present invention, an ion generating unit 40 in which the plurality of ion generating sections 41 are integrated with each other, the ion generating unit 40 being attachable to and detachable from a fan cover 50 while the plurality of ion generation parts are being integrated with each other.

The above configuration makes it possible to safely and easily detach the ion generating unit 40, in which the plurality of ion generating sections 41 are integrated with each other, from the fan cover 50 during their cleaning and/or maintenance.

An ion generator 1 in accordance with a fourth aspect of the present invention further includes, in the third aspect of the present invention, a housing (upper cover 10) in which the fan cover 50 is housed, the fan cover 50 being attachable to and detachable from the housing (upper cover 10) while the ion generating unit 40 is being attached to the fan cover 50.

The above configuration makes it possible to safely and easily detach the fan cover 50, to which the ion generating unit 40 in which the plurality of ion generating sections 41 are integrated is attached, from the housing (upper cover 10) during their cleaning and/or maintenance.

An ion generator 1 in accordance with a fifth aspect of the present invention further includes, in any one of the first aspect through the fourth aspect of the present invention, a lighting member 90 configured to emit light towards the side of the first direction.

The above configuration allows the ion generator 1 to have a function of a lighting device.

An ion generator 1 in accordance with a sixth aspect of the present invention includes, in any one of the first aspect through the fifth aspect of the present invention, the control substrate 30 having a control section configured to control the fan 33 and the ion generating section 41 to operate and the motor 31 configured to cause the fan 33 to rotate, wherein the control substrate 30 is provided so as to be closer to the side of the second direction than the fan 33, the motor 31 is attached in a through hole provided at a center part of the control substrate 30, and the ion generating section 41 is provided so as to be parallel to the radial direction of the fan 33 with respect to the control substrate 30.

Note that the ion generating section 41 includes a needle-shaped electrode 41*a* having a pointed tip, wherein the tip of the electrode 41*a* points so as to be substantially parallel to the rotational axis direction of the fan 33.

The above configuration makes it possible to concentrically provide the control substrate 30, the motor 31, and the ion generating section 41 in a direction parallel to the radial direction of the fan 33 without overlapping each other. This makes it possible to further reduce the fan 33 of the ion generator 1, in the axial direction, in thickness, and ultimately makes it possible to further downsize the ion generator 1.

In the above configuration, the control substrate and the ion generating section are provided concentrically around the motor, which is the heaviest component of the ion generator. This makes it easier to cause the ion generator to have a weight balanced in vertical and horizontal directions. Furthermore, the motor is provided so as to be near to the duct plug 20 which is configured to hang from a ceiling. This makes it possible to reduce torque to be applied to an engaging part 20*b* of the duct plug 20 even in a case where the ion generator is shaken right and left, and ultimately allows the ion generator to have a shock-resistant structure.

In the above configuration, an PCI unit 40 has an inner diameter greater than an outer diameter of the fan 33. This makes it possible to safely and easily detach the PCI unit 40 without detaching the fan 33 when the ion generating section 41 is being cleaned or replaced.

An ion generator 1 in accordance with a seventh aspect of the present invention further includes, in any one of the first aspect through the sixth aspect of the present invention, a lower cover 70 attached to the fan cover 50 on the side of the first direction and having an opening 72 whose shape matches a suction opening 51 of the fan cover 50, the fan cover 50 having the suction opening 51 via which external air is sucked in and which is provided on the side of the first direction so as to face the fan 33, a filter 60 provided so as to cover the opening 72, and a bottom plate 80 attached to the lower cover 70 on the side of the first direction so that a gap via which external air is sucked in is provided between the bottom plate 80 and the lower cover 70, the bottom plate 80 having an outer diameter greater than an outer diameter of the filter 60, the lower cover 70, the filter 60, and the bottom plate 80 being integrally attachable to and detachable from the fan cover 50.

In the above configuration, (i) the lower cover 70, the filter 60, and the bottom plate 80 are integrally attachable to and detachable from the fan cover 50, and (ii) the bottom plate 80 having an outer diameter greater than that of the filter 60 is provided below the filter 60. This makes it possible to prevent, when those components are being attached or detached, dust or the like adhering to the filter from falling.

An ion generator 1 in accordance with a eighth aspect of the present invention is arranged such that, in the seventh aspect of the present invention, a rim part 81 of the bottom plate 80 is warped or bent towards the side of the first direction.

In the above configuration, the rim part 81 of the bottom plate 80 is warped or bent towards the side of the first direction. This makes it possible to more efficiently prevent dust or the like adhering to the filter 60 from falling.

An ion generator 1 in accordance with a ninth aspect of the present invention is arranged such that, in the seventh aspect or the eighth aspect of the present invention, at least one of the fan cover 50 and the lower cover 70 has a guide 50*d* which is configured to regulate, when the lower cover 70, the filter 60, and the bottom plate 80 are being attached to or detached from the fan cover 50, respective movement directions of the lower cover 70, the filter 60, and the bottom plate 80.

In the above configuration, the guide 50*d* regulates, when the lower cover 70, the filter 60, and the bottom plate 80 are being attached to or detached from the fan cover 50, the respective movement directions of them. This makes it possible to more efficiently prevent dust or the like adhering to the filter 60 from falling.

An ion generator 1 in accordance with a tenth aspect of the present invention includes, in any one of the first aspect through the ninth aspect of the present invention, a duct plug 20 via which the ion generator 1 is connected to the wiring duct 110, the duct plug 20 being provided so as to be closer to the side of the second direction than the fan 33.

The above configuration makes it possible to connect the ion generator 1 to a wiring duct 110 by using the duct plug 20.

An ion generator 1 in accordance with an eleventh aspect of the present invention further includes, in the tenth aspect of the present invention, a dummy duct plug 21 via which the ion generator 1 is non-electrically connected to the wiring duct 110, wherein the ion generator 1 is electrically connected to the wiring duct 110 via the duct plug 20 so that the ion generator 1 is electrified via the wiring duct 110.

The above configuration makes it possible to stabilize connection between the wiring duct 110 and the ion generator 1 by using the dummy duct plug 21, as compared with the case where a wiring duct 110 is connected to an ion generator 1 via a single duct plug 20.

The above configuration makes it possible to hang the ion generator 1 from the wiring duct 110 with larger force by using the dummy duct plug 21, as compared with the case where an ion generator 1 is connected to a wiring duct 110 via a single duct plug 20. This ultimately makes it possible to reduce a risk of the ion generator 1 falling even in a case where the ion generator 1 is shaken by earthquakes or the like.

The present invention is not limited to the description of the embodiments above, but may be altered by a skilled person within the scope of the claims. Any embodiment based on a proper combination of technical means disclosed in different embodiments is also encompassed in the technical scope of the present invention. Further, a new technical feature can be achieved by combining technical means disclosed in different embodiments.

INDUSTRIAL APPLICABILITY

The present invention is applicable to an ion generator.

REFERENCE SIGNS LIST

1 Ion generator
10 Upper cover (housing)
20 Duct plug
21 Dummy duct plug
30 Control substrate
31 Motor (fan driving part)
32 Substrate holder
33 Fan (centrifugal fan)
40 PCI unit (ion generating unit)
41 Ion generating section
50 Fan cover
50*a* Upper surface part
50*b* Side surface part
50*c* Bottom surface part
50*d* Guide
51 Suction opening
52 First air flow path
53 Second air flow path
54 Discharge opening
60 Filter
70 Lower cover
72 Opening
73 Rim part
74 Guided surface
80 Bottom plate
81 Rim part
90 Lighting member
110 Wiring duct

The invention claimed is:
1. An ion generator, comprising:
a fan configured to send sucked air;
one or more ion generating modules each configured to generate ions in the sucked air sent by the fan, wherein the one or more ion generating modules each include an electrode that generates ions;
a motor configured to cause the fan to rotate;
a control substrate being a plate-like substrate and configured to control at least the motor and the one or more ion generating modules; and
a duct plug via which the ion generator is connected to a wiring duct, the duct plug being provided so as to be located above the fan such that the ion generator is configured to hang from the ceiling,
the control substrate and the one or more ion generating modules being provided on a single plane which is parallel to a radial direction of the fan, the radial direction being perpendicular to a rotational axis direction of the fan, the control substrate and the one or more ion generating modules being provided concentrically around the motor, the motor being attached in a through hole provided at a center part of the control substrate.
2. An ion generator as set forth in claim 1, further comprising:

a fan cover which houses the fan therein and which forms an air flow path through which air sent by the fan is guided, the fan cover having an opening via which the one or more ion generating modules are exposed to the air flow path.

3. An ion generator as set forth in claim 2, wherein the one or more ion generating modules are two or more ion generating modules, the two or more ion generating modules are provided on a single member and thereby constitute an ion generating unit, and the ion generating unit is attachable to and detachable from the fan cover.

4. An ion generator as set forth in claim 3, further comprising:

a housing in which the fan cover is housed, the fan cover being attachable to and detachable from the housing while the ion generating unit is being attached to the fan cover.

5. An ion generator as set forth in claim 2, further comprising:

a lower cover attached to the fan cover and the lower cover having an opening whose shape matches a suction opening of the fan cover, the fan cover having the suction opening via which external air is sucked in, and which face the fan;

a filter provided so as to cover the opening of the lower cover; and a bottom plate attached to the lower cover such that a gap via which external air is sucked in is provided between the bottom plate and the lower cover, the bottom plate having an outer diameter greater than an outer diameter of the filter, the lower cover, the filter, and the bottom plate being integrally attachable to and detachable from the fan cover.

* * * * *